US006418930B1

(12) United States Patent
Fowler (10) Patent No.: US 6,418,930 B1
(45) Date of Patent: Jul. 16, 2002

(54) ANATOMIC INCONTINENCE PESSARY

(75) Inventor: Robert Stuart Fowler, Scottsdale, AZ (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 44 days.

(21) Appl. No.: 09/712,737

(22) Filed: Nov. 14, 2000

(51) Int. Cl.[7] .................................................. A61F 6/06
(52) U.S. Cl. ........................ 128/830; 128/834; 128/885
(58) Field of Search ................................ 128/830–841, 128/885

(56) References Cited

U.S. PATENT DOCUMENTS

| | | | | |
|---|---|---|---|---|
| 14,293 A | * | 2/1856 | Roesler | 128/834 |
| 183,832 A | * | 10/1876 | Barnett | 128/834 |
| 604,958 A | * | 5/1898 | Biesmeyer | 128/834 |
| 1,750,188 A | * | 3/1930 | Mumberg | 128/834 |
| 4,307,716 A | * | 12/1981 | Davis | 128/834 |
| 5,771,899 A | * | 6/1998 | Martelly | 128/830 |

* cited by examiner

*Primary Examiner*—Michael A. Brown
(74) *Attorney, Agent, or Firm*—Gregory F. Cotterell (57) ABSTRACT

An incontinence pessary device for use within a vaginal vault of a woman, the incontinence pessary device comprising a resilient main support body, at least two resilient lateral support bodies, and a suburethral support body. The resilient main support body has a primary plane of orientation that will correspond to the sagittal plane of the woman's pelvis when inserted and be at least responsive to forces oriented along the main plane. The at least two resilient lateral support bodies project from a position on the main support body toward generally opposite sides of the main support body in a secondary plane generally perpendicular to the primary plane. Thus, when inserted, the at least two resilient lateral support bodies provide lateral and additional rotational stabilization, being at least responsive to forces oriented along the secondary plane. The suburethral support body has a longitudinal axis of orientation in the primary plane, which forms an obtuse angle to the secondary plane, and has a surface, elongated along the longitudinal axis, for engaging the mucosa and periurethral tissues of the vaginal vault of the woman when placed in position within the woman's vaginal vault. The suburethral support body projects from a position on the main support body generally opposite the position of projection for the at least two lateral support bodies.

32 Claims, 4 Drawing Sheets

ANATOMIC INCONTINENCE PESSARY

FIELD OF THE INVENTION

This invention relates to an incontinence pessary having a shape more closely resembling the anatomic conformation of the vaginal vault. More specifically, the invention provides a design that confers stabilization in all three of the vaginal axes, the longitudinal axis, the antero-posterior axis, and the lateral axis, as well as, stabilization against rotation around these axes. In addition, the invention more specifically provides for an expanding flexible segment and/or electrode surface for engaging the periurethral tissue of the antero-superior vaginal vault.

BACKGROUND OF THE INVENTION

Pelvic floor relaxation in women, as a natural result of childbirth, age and anatomic predisposition, often results in prolapse of one or more of the various organs within the pelvis, such as the uterus, urinary bladder, rectum and intestines. In particular, relaxation of the support to the urinary bladder and the urethra often results in urinary incontinence. Typically, this urinary incontinence is a form known as stress incontinence that results in leakage of urine at times of physical stress that suddenly increase the intraabdominal pressure, such as coughing, laughing, sneezing, or physical exercise.

Stress incontinence is not only a medical problem for the woman, but also creates social difficulty, as well. Inappropriate urine leakage may result in perineal skin maceration and skin breakdown, which can be further complicated by bacterial and fungal infection. In addition, the woman's clothing becomes soiled and emanates characteristic urine malodor unless steps are taken to absorb the urine in devices such as pads or incontinence diapers.

A common solution to the problem of pelvic relaxation is the use of a pessary inserted within the vaginal vault. A number of different types of pessaries are available, ranging from cubes, doughnuts, rings, and discs, to blocks of material, each completely, or at least partially inserted within the vaginal vault. Pessaries having inflatable portions are also contemplated. In all cases, the pessary acts as a vaginal space-occupying device intended to support the organs and tissues of the pelvis when the woman's own anatomic suspension has failed. Consequently, a pessary is subjected to prolong use and must maintain its positioning and support continuously while not interfering with normal activities of daily living. Additionally, there have been several pessaries designed for the treatment of urinary stress incontinence. These have not achieved their desired effect because they are not stable in all axes of vaginal orientation. Lack of stability in all axes allows for off axis forces to be applied to these pessaries, which causes misdirection of the force to the periurethral tissue and urethra relied on for continence by these devices.

However, the type and extent of pelvic relaxation and subsequent prolapse of any one or more organs and the degree of urinary incontinence encountered is highly variable from one woman to the next. Unfortunately, current pessary styles may provide relief for a particular aspect of the problem, but do not provide for adequate problem solving for all the difficulties encountered. As an example, a pessary may be well adapted for support of a prolapsing rectum, but is inefficient at providing simultaneous urethral support for control of stress incontinence. The rectum, uterus, and urinary bladder are midline anatomic structures that generally prolapse in the midline, or sagittal plane. The prolapsing organ places antero-posterior, longitudinal, lateral and/or rotational displacement forces on any pessary placed within the vaginal vault. When not stabilized against all of these forces, a pessary becomes displaced. This displacement of the pessary defeats the pessary's function in controlling urinary incontinence by failing to support the urethra.

What is needed is an incontinence pessary that is anatomic in its orientation to various pelvic structures, providing continuous support of these organs. Such a pessary will also provide continuous control of urinary incontinence, provide for proper release of vaginal secretions, and not interfere with normal daily activities.

SUMMARY OF THE PRESENT INVENTION

The present invention contemplates an incontinence pessary device for use within a vaginal vault of a woman that comprises a resilient main support body, at least two resilient lateral support bodies, and a suburethral support body. The main support body is generally a disc or torus shape of resilient material, the disc having a primary plane of orientation. The disc or torus shape provides for a differential response to compressive forces, particularly to forces applied to the disc or torus along the primary plane of the disc or torus.

As contemplated by the present invention, the main support body, when inserted in the vagina will be oriented with the plane of the disc or torus oriented to the sagittal plane of the woman's pelvis. Thus, the main support body is in a position to counter the effects of any prolapsing organ, such as the urinary bladder, uterus or rectum into the vaginal vault. The prolapse movement of any of these organs will exert a compressive force on the main support body that is in the primary plane of the main support body. The orientation of such compressive forces may be any of the sagittal plane axes of orientation: antero-posterior, cephalo-caudal, and longitudinal, i.e., along the long axis of the vaginal vault. These forces are readily countered by the resiliency of the material used in the main support body.

A tendency for some pessaries, after placement in the vaginal vault, is to shift laterally or rotate out of position when encountering the forces applied to it along the sagittal plane. The present invention uses at least two resilient lateral support bodies to effectively counter this effort. The present invention contemplates that the lateral support bodies will be provided as opposing pairs, but the number of pairs used is not limited. The Description and Figures provided herein disclose the use of two lateral support bodies, although, any number of pairs may be used depending upon the degree of stabilization sought.

The lateral support bodies project at an angle from a position on the main support body toward generally opposite sides of the main support body. Each lateral support body generally sweeps backward and outward from the primary plane of the main support body. Each pair of lateral support bodies forms a secondary plane generally perpendicular to the primary plane. Thus, when the pessary of the present invention is placed within the vaginal vault, the lateral support bodies project posteriorly within the vaginal vault, and laterally from the sagittal plane of the pelvis. The ends of the lateral support bodies will abut the posterio-lateral vaginal wall with the rectum between the lateral supports.

The lateral support bodies also demonstrate a differential response to the compressive forces, the lateral support bodies being stiffer along their length than across their width. Forces that would tend to push the pessary laterally will be generally exerted along the secondary plane of each pair of lateral support bodies used. The lateral support bodies stabilize the pessary of the present invention by countering any tendency for the pessary to want to move laterally out of the way of a any prolapsing organ.

Additionally, the lateral support bodies stabilize the pessary in the anterop osterior axis keeping the suburethral support body intimately adjacent the mucosa of the periurethral tissues. The lateral support bodies are stiffer along the secondary plane in this antero-posterior axis and contribute directly to the pressure applied by the suburethral support body to the woman's urethra to control incontinence. Note that either lateral forces or antero-posterior forces exerted on the lateral support bodies are designed to meet the lateral support bodies at oblique angles, limiting the mechanical advantage that might be encountered if met end on. This will ensure that there will always be some give in the lateral support bodies t o avoid inadvertent excessive forces that may be encountered, such as during a cough. Lastly, the lateral support bodies stabilize the present invention against rotational forces, especially limiting rotation around the lateral and longitudinal axes.

The suburethral support body is an elongate structure having its longitudinal axis laying within the primary plane of the main support body. The suburethral support body projects from a position on the main support body that is generally, but not necessarily, opposite the position from which the lateral support bodies arise. The longitudinal axis lays at an angle to the secondary plane of the lateral support bodies. Ideally this angle is an obtuse angle as measured going counter clockwise from the lateral support body position on the main support body. The angulation of the longitudinal axis of the suburethral support body in relation to the secondary plane of the lateral support bodies further stabilizes the device of the present invention against rotational forces, particularly stabilizing against rotation about the longitudinal and antero-posterior axes.

The present invention anticipates the use of a contact surface area oriented along the suburethral support body for directly abutting the mucosa of the periurethral tissues. This direct abutment provides the pressure to a substantial length of the urethra needed to achieve the continence control. The elongated nature of this abutment surface provides for a significant amount of surface area from which to deliver the pressure to the urethra. Spreading the pressure over a large area markedly decreases the likelihood of point pressure occurring and subsequent pain and tissue necrosis.

The urethra in the female lays along the sagittal plane and within the periurethral tissues in the superior wall, or roof of the distal portion of the vaginal vault. The course of the urethra is evident by a raised ridge in the surface of the mucosa of the vagina. The contact surface area of the suburethral support body may be improved by the addition of lateral prominences running substantially the length of the suburethral support body. These prominences are lateral to either side of the contact surface area and create a hollow, or recess, with the suburethral support area therebetween for the urethra to lay in. Thus, with the lateral prominences, the contact surface area will more closely approximate the geometry of the periurethral tissues and urethra, improving the overall contact and dispersion of continence efforts. These lateral prominences also contribute to stabilization of the present invention, particularly stabilization against rotation around the longitudinal axis.

The present invention further anticipates the use of an expansion membrane controllable by the woman. This may take the form of an inflatable chamber having a distendable membrane along the area of the contact surface. After placement of the pessary, the woman may apply increased continence effort by inflating this chamber with a suitable fluid medium. The woman may adjust the amount of inflation and, consequently, the amount of continence effort applied by the pessary to achieve the desired effect.

The present invention also contemplates the use of electrical stimulation applied directly to the periurethral tissues and urethra by electrodes carried on the contact surface. The electrical stimulation is used to create increased tone within the musculature of the periurethral tissue and the urethra directly. This increase muscular tone provides added continence control. Electrical stimulation capability also may be combined with the inflatable chamber and distendable membrane to further increase the range of continence control capability. In addition, having the various modalities contained within one pessary provides for the woman to alternate between the modalities.

The above and other objects and advantages of the present invention become more readily apparent when reference is made to the following detailed description taken in conjunction with the accompanying drawings. The following descriptions are in no way intended to limit the scope of the present invention.

DETAILED DESCRIPTION OF THE INVENTION

Figures 1, 2, 3:
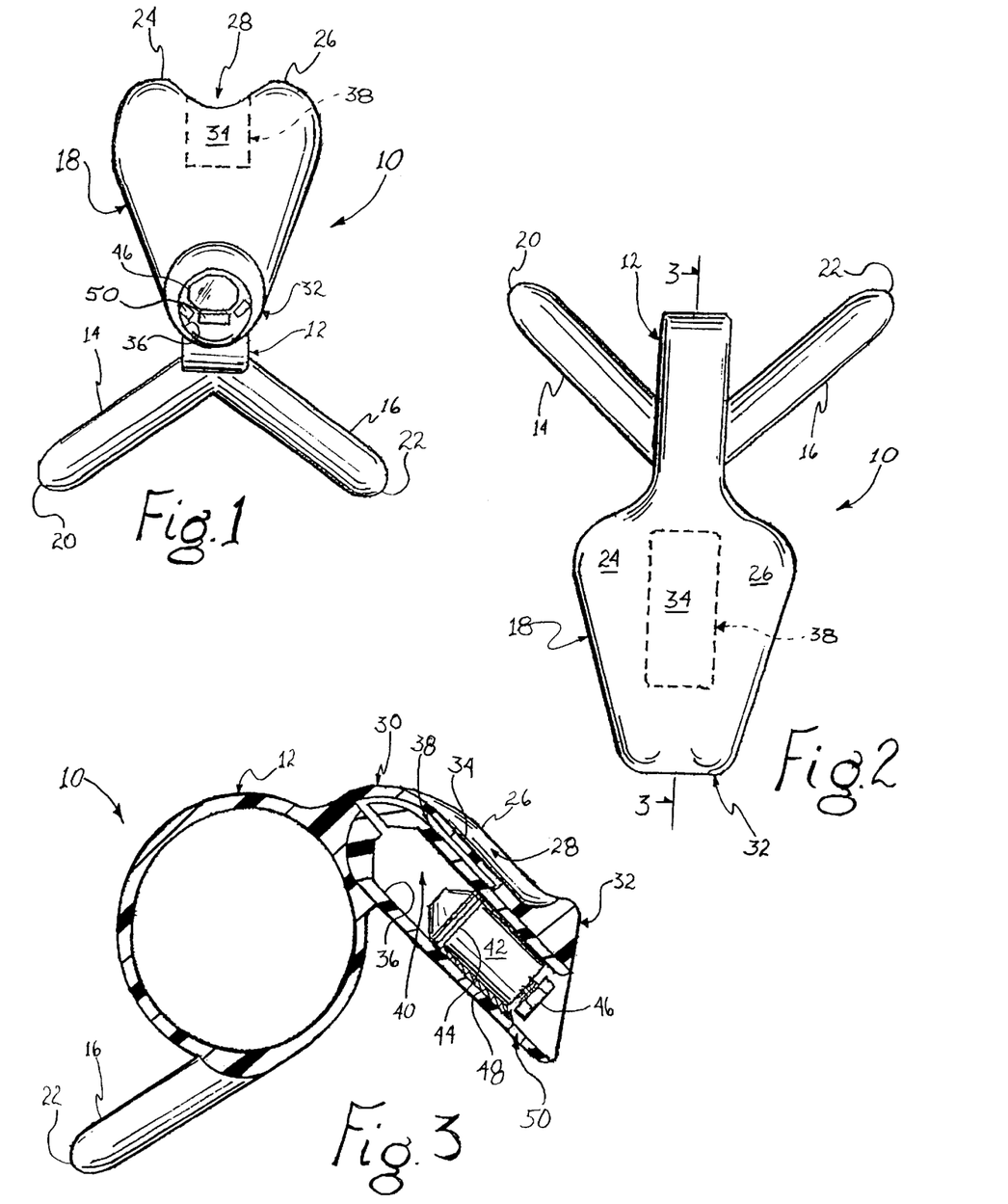
FIG. 1 is a front elevational view of an embodiment of the present invention.
FIG. 2 is a top view of the embodiment depicted in FIG. 1.
FIG. 3 is a cross-sectional view of the embodiment of FIG. 1 taken along the line 3—3 of FIG. 2.

Referring to FIGS. 1 through 3, wherein like numbers depict like components through out the various Figures, there is depicted an anatomic incontinence pessary device 10 comprising a main support body 12, a lateral support body 14, a lateral support body 16, and a suburethral support body 18. Main support body 12 is a ring or torus structure having a primary plane of orientation. Lateral support bodies 14, 16 project laterally and posteriorly at an angle from main support body 12 ending in tips 20, 22, respectively. The projecting lateral support bodies 14, 16 form a secondary plane that is perpendicular to the primary plane of main support body 12.

Suburethral support body 18 includes periurethral prominences 24, 26, a suburethral depression 28 laying as a hollow from an end 30 to an end 32 and between periurethral prominences 24, 26, a distendable membrane 34, an inner cylinder 36, an expansion space 38, an inner chamber 40, an adjustable plunger 42, an "O" ring seal 44, an adjusting nut 46, a ratchet and pawl 48, and at least one mucous vent 50. Suburethral support body 18 has a general longitudinal axis laying in the general orientation parallel to the orientation from end 30 to end 32. Suburethral support body 18 projects from main support body 12 at a position generally, but not necessarily exactly, opposite from the position from which lateral support bodies 14, 16 project from main support body 12. The position on main support body 12 from which suburethral body 18 projects may be anywhere from about 90° to about 270° counter-clockwise from the position that lateral bodies 14, 16 project from, as viewed in FIG. 3. Additionally, the longitudinal axis of suburethral body 18 lies within the primary plane of main support body 12 and at an obtuse angle to the secondary plane of lateral support bodies 14, 16. This angle is greater than 90° and less than 180°, and preferably is from about 95° to about 135°. Adjustable plunger 42 operably engages inner cylinder 36 with ratchet and pawl 48. Adjustable plunger 42 may be incrementally moved telescopically within inner cylinder 36, held at each incremental step by the pawl. The pawl may be disengaged by gripping and turning adjusting nut 46. Alternative to this arrangement is the use of an extension arm from the pawl instead of the nut, not shown, that may be depressed to effect release of the pawl from the ratchet. Another alternative to the ratchet and pawl, but not shown, are mated threaded surfaces for the plunger and inner cylinder.

Pessary device 10 is preferably constructed from a polymer. Any number of polymers and co-polymers are useful in the medical arts. Such polymers and co-polymers have the characteristics of being biocompatible, hypoallergenic, and easily cleaned. In addition, there may also be the need for a pessary durable enough to withstand the rigors of sterilization, whether by autoclave or ethylene oxide. A number of such useful polymers are, by way of example, the "hard" elastomeric silicones, polyethylene, polypropylene, polyester, polyurethane, poly(vinyl chloride), polyisobutylene, polychloroprene, polystyrene, and polybutadiene, and their co-polymers, to name a few. Preferably, main support body 12 and lateral supports 14, 16 are made as a unitary structure out of a resilient polymeric compound having sufficient elastic properties to allow for bending and/or folding to facilitate insertion into the vagina, yet sufficiently stiff to provide elastic support to the surrounding tissues after insertion. Preferably, main support body 12 and lateral supports 14, 16 are made from "hard" elastomeric silicone, such as silastic. Another polymer useful in this capacity is polyurethane.

Likewise, preferably the outer surface of suburethral support body 18 is constructed with the same elastic material as main support body 12. Preferably, this is a "hard" elastomeric silicone or resilient polyurethane. An elastomeric polymer is particularly useful for distendable membrane 34. The outer surface of suburethral support body 18 and distendable membrane 34 may be incorporated into main support body 12 in a unitary construction, or may be fused or glued together from individual components.

Inner cylinder 36 may be manufactured from any number of polymeric compounds useful in the medical arts, such as polyethylene, polypropylene, polyester, polyurethane, poly(vinyl chloride), polyisobutylene, polychloroprene, polystyrene, and polybutadiene, to name a few. Particularly useful polymers are polyester, polypropylene and poly(vinyl chloride). Inner cylinder 36 may be constructed from a rigid polymeric compound from any one or more of the above mentioned polymers, their co-polymers, or from metals or metal alloys, such as stainless steel or other similarly medically useful metals, or even from ceramics. Alternatively, inner cylinder 36 may be constructed with a semi-rigid polymeric compound, or even a resilient polymeric material that is then augmented with implanted metal or metal alloy rings, bands, or rods, that are themselves resilient or spring-like. See FIG. 9.

The purpose of inner cylinder 36 is to house adjustable plunger 42 within inner chamber 40. Adjustable plunger 42 slidably, telescopically engages the inside surface of inner cylinder 36 with "O" ring seal 44 creating inner chamber 30 that is in fluid communication with expansion space 38 beneath distendable membrane 34. Inner chamber 40 may filled with air, water, oil, gel, or other suitable fluid compound that is useful in medical applications. Moving adjustable plunger 42 in or out of inner cylinder 36 applies or releases pressure to the fluid medium within inner chamber 40. As pressure is applied, the fluid medium is pushed out of inner chamber 40 into expansion space 38 beneath distendable membrane 34. The elastic properties of distendable membrane 34 provide for distendable membrane 34 to expand outwardly into suburethral depression 28, gradually filling this depression as more pressure is applied through the movement of adjustable plunger 42 within inner cylinder 36. When the pressure applied by adjustable plunger 42 is released by turning adjusting nut 46 to disengage ratchet and pawl 48, fluid medium may be drawn back into inner chamber 40 from expansion space 38 beneath distendable membrane 34. With this release of pressure, distendable membrane 34 elastically returns to its non-distended position as the floor of suburethral depression 28. In an anticipated alternative form where the plunger and inner cylinder wall are engaged by threaded screw, screwing in out the plunger provides smoother control than the incremental jumps encountered with the ratchet and pawl.

In operation, and by way of example, pessary device 10 is positioned into a woman's vaginal vault such that pessary device 10 will be oriented within the woman's vaginal vault with suburethral support body 18 anterior to main support body 12 and lateral support bodies 14, 16 extend laterally and posteriorly from main support body 12, being somewhat inferior to main support body 12. End 30 of suburethral support body 18 is positioned proximate the woman's vesico-urethral junction and end 32 is at the introitus of the vagina. This mode of insertion and the subsequent positioning of pessary device 10 also are representative of the insertion and positioning for the alternative embodiments of pessary devices 60 and 100 of the present invention.

Insertion is easily accomplished by displacing main support body 12 and approximating lateral support bodies 14, 16 into an elongated configuration along the longitudinal axis of suburethral support body 18. Insertion is then accomplished by inserting the axially aligned device along the axis of the vaginal vault, releasing the various components as the device is inserted. When properly inserted, the primary plane of main body 12 lies on the midline or sagittal plane of the woman's pelvis, with the longitudinal axis of suburethral support body 18 also aligned along the midline of the woman's vaginal vault. The woman's urethra lies within suburethral depression 28 and is bounded laterally by periurethral prominences 24, 26. Main support body 12 positioning in the midline, vertically oriented position provides vertical, longitudinal and antero-posterior stabilization to the various midline organs. Lateral support bodies 14, 16 project posteriorly and laterally in the secondary plane, straddling the rectum between them. This provides for additional antero-posterior stabilization, as well as, lateral and rotational stabilization. The secondary plane of lateral support bodies 14, 16 forms an obtuse angle with the longitudinal axis of suburethral support body 18 providing additional antero-posterior and longitudinal stabilization within the vagina. Lastly, periurethral prominences 24, 26 provide additional rotational and lateral stabilization with the urethra within suburethral depression 28. The sum total of all of this positional and orientation stabilization keeps distendable membrane 34 abutting periurethral tissue. Thus, suburethral support body 18 remains in proper alignment with the woman's urethra, providing secure adjustable pressure to the urethra and, ultimately, urinary continence.

Once positioned, the woman may now use a convenient tool or her fingers to manually depress adjustable plunger 42 within inner cylinder 36 to effect expansion of distendable membrane 34 and apply appropriate direct pressure to the woman's urethra along a substantial length of the urethra. The pressure applied by distendable membrane 34 is spread out over a substantial surface area to limit the occurrence of any pressure points that might lead to discomfort or tissue damage.

The amount of pressure applied to distendable membrane 34 can be individually adjusted so that a woman may void on volition, or potentially apply enough pressure to completely eliminate any form of incontinence, including urge episodes. In the latter case, when the woman wishes to micturate, she may need to release adjustable plunger 42 from ratchet and pawl 48 allowing the pressure to be released, the fluid to flow back to inner chamber 40, and distendable membrane 34 to retract back into suburethral depression 28 releasing the pressure on the woman's urethra. In addition, at least one mucous vent 50 provides for the appropriate drainage of vaginal mucous secretions. A woman using the present invention may wear it comfortably for considerable time periods, both night and day without the device of the present invention interfering with normal daily activities.

Figure 4:
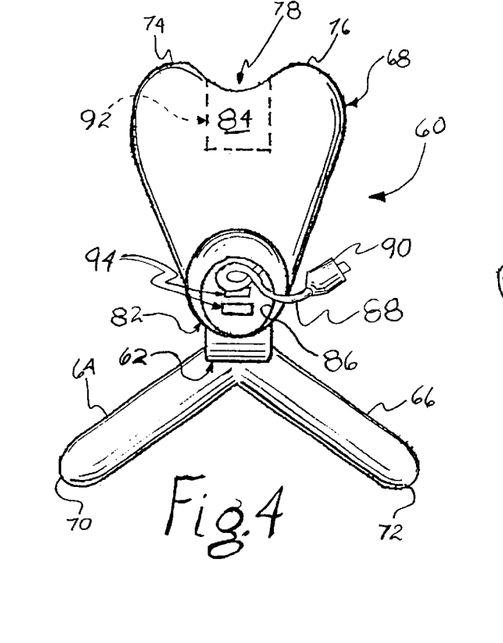
FIG. 4 is a front elevational view of an alternate embodiment of the present invention depicting an alternate mechanism for inflating the suburethral support membrane.
Figure 5:
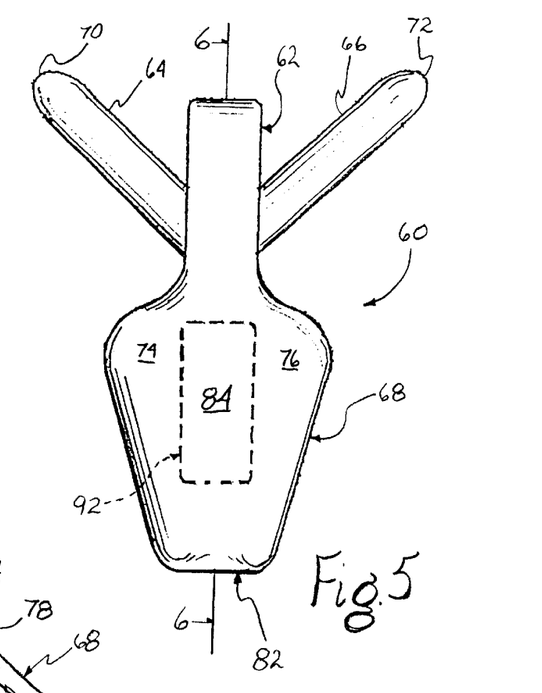
FIG. 5 is a top view of the embodiment depicted in FIG. 4.
Figure 6:
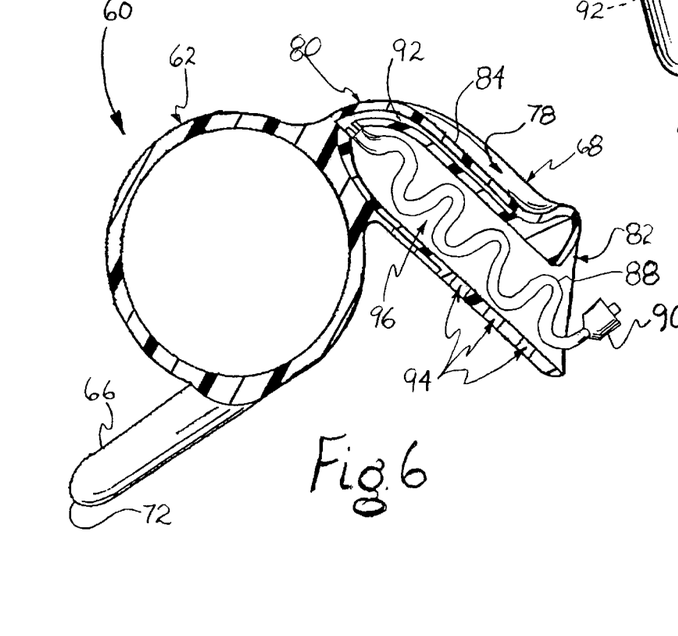
FIG. 6 is a cross-sectional view of the embodiment of FIG. 4 taken along the line 6—6 of FIG. 5.

Referring to FIGS. 4–6, there is depicted an alternative, yet preferred, embodiment of the present invention in an anatomic incontinence pessary device 60 comprising a main support body 62, a lateral support body 64, a lateral support body 66, and a suburethral support body 68. Main support body 62 is a ring or torus structure having a primary plane of orientation. Lateral support bodies 64, 66 project laterally and posteriorly at an angle from main support body 62 ending in tips 70, 72, respectively. The projecting lateral support bodies 64, 66 form a secondary plane that is perpendicular to the primary plane of main support body 62.

Suburethral support body 68 includes periurethral prominences 74, 76, a suburethral depression 78 laying as a hollow from an end 80 to an end 82 and between periurethral prominences 74, 76, a distendable membrane 84, an inner cylinder 86, a tube 88 with a valve 90 at one end and fluidly connected to an expansion space 92 at its other end, and at least one mucous vent 94. Inner cylinder 86 includes an inner chamber 96 within which tube 88 and valve 90 may course. Suburethral support body 68 has a general longitudinal axis laying in the general orientation parallel to the orientation from end 80 to end 82.

Suburethral support body 68 projects from main support body 62 at a position generally, but not necessarily exactly, opposite from the position from which lateral support bodies 64, 66 project from main support body 62. The position on main support body 62 from which suburethral body 68 projects may be anywhere from about 90° to about 270° counter clock-wise from the position from which lateral bodies 64, 66 project, as viewed in FIG. 6. Additionally, the longitudinal axis of suburethral body 68 lies within the primary plane of main support body 62 and at an obtuse angle to the secondary plane of lateral support bodies 64, 66. This angle is greater than about 90° and less than about 180°, and preferably is from about 95° to about 135°. The components of pessary device 60 may be constructed from the various materials listed above for pessary device 10, and, for the sake of brevity, are incorporated here by reference.

In this embodiment, the plunger and ratchet and pawl, or threaded plunger, are replaced with tube 88 with valve 90. The tube is preferably made from a polymer, such as the polymers listed above that is suitable for use in medical device applications. A preferred application for tube 88 is that the tube have a degree of coiling hysteresis incorporated into its resiliency providing for tube 88, with valve 90, to recoil into inner chamber 96 when not in use. Valve 90, preferably, incorporates a "luer" lock, which is suitable for engagement with standard medical syringes for inflating and deflating expansion space 92.

In use, the woman inserts pessary device 60 in the same fashion as described for pessary device 10, with the primary plane in the sagittal plane of the woman's pelvis, end 80 proximate the vesico-urethral junction, and end 82 proximate the introitus of the vagina. Pessary device 60, having the same basic structural design, also has the same orientation stability in all planes and axes as discussed above for pessary device 10. Urethral continence pressure is applied by the woman using an appropriate syringe to fill expansion space 92 beneath distendable membrane 84 with an appropriate fluid medium and applying direct pressure to the woman's urethra. The woman may use any number of different fluid mediums, such as air, water, gel or oil. After filling, tube 88 and valve 90 may self retract out of the way in inner chamber 96.

The pressure applied by distendable membrane 84 is spread out over a substantial surface area to limit the occurrence of any pressure points that might lead to discomfort or tissue damage. The amount of pressure applied to distendable membrane 84 can be individually adjusted so that a woman may void on volition, or potentially apply enough pressure to completely eliminate any form of incontinence, including urge episodes. In the latter case, when the woman wishes to micturate, she may need to release fluid back into a syringe allowing distendable membrane 84 to retract back into suburethral depression 78, releasing the pressure on the woman's urethra. In addition, at least one mucous vent 94 provides for the appropriate drainage of vaginal mucous secretions.

Figure 7:
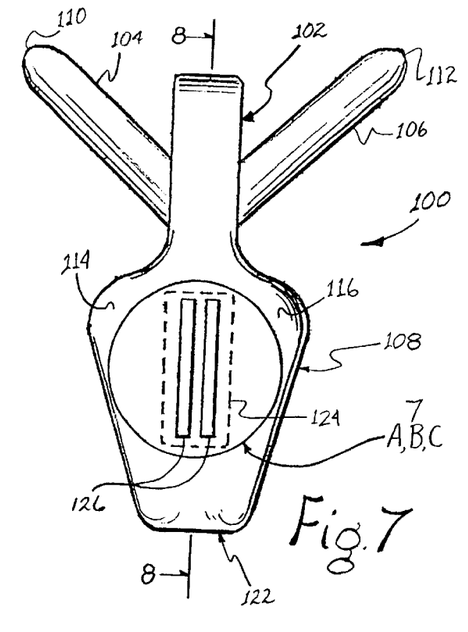
FIG. 7 is a top plan view of another alternate embodiment of the present invention demonstrating deployment of a set of electrodes.
Figures 7A, 7B:
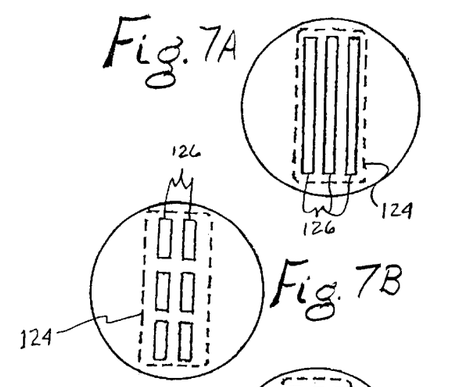
FIGS. 7A, 7B, and 7C are top plan views of additional alternate embodiments of the embodiment of FIG. 7 demonstrating additional patterns of deployment for various sets of electrodes.
Figure 7C:
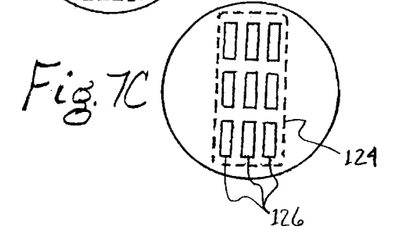
Figure 8:
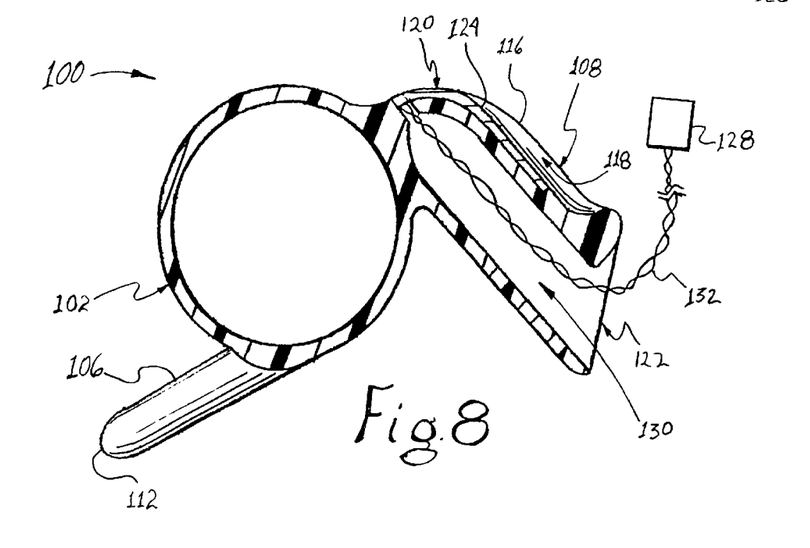
FIG. 8 is a cross-sectional view of the embodiment of FIG. 7 taken along the line 8—8 of FIG. 7.

In reference to FIGS. 7–8, there is depicted an alternative embodiment to the present invention as an anatomic incontinence pessary device 100 comprising a main support body 102, lateral support bodies 104, 106, and a suburethral support body 108. Main support body 102 is a ring or torus structure having a primary plane of orientation. Lateral support bodies 104, 106 project laterally and posteriorly at an angle from main support body 102 ending in tips 110, 112, respectively. The projecting lateral support bodies 104, 106 form a secondary plane that is perpendicular to the primary plane of main support body 102.

Suburethral support body 108 includes periurethral prominences 114, 114, a suburethral depression 118 laying as a hollow from an end 120 to an end 122 and between periurethral prominences 114, 116, and an electrode surface 124 having an electrode array 126 with at least two electrodes. Electrode array 126 is depicted in the various Figures, including FIGS. 7A, B, and C as comprising a plurality of electrodes. The number and pattern of the electrodes is not to be construed as limited by only those patterns depicted. In this embodiment, pessary device 100 uses appropriate electrical stimulation of the urethra and the vesico-urethral junction to increase periurethral muscle tone and strength. A power source and control circuit 128 may be housed within a cavity 130 of suburethral support body 108, much in the same area as the inner chamber of the previously depicted devices of this invention, with electric wires 132 appropriately embedded within the housing of the device. Alternatively, suburethral support body 108 may be solid or hollow, and there may be a power pack worn on the woman's belt or similar area. The woman's access to the control circuit is much the same as for the previously depicted devices. The components of pessary device 100 may be constructed from the various materials listed above for pessary device 10, and are incorporated by reference here for the sake of brevity.

In use, the woman inserts pessary device 100 in the same fashion as described for pessary devices 10 and 60, above, with the primary plane in the sagittal plane of the woman's pelvis, end 120 proximate the vesico-urethral junction, and end 122 proximate the introitus of the vagina. Pessary device 100, having the same basic structural design, also has the same orientation stability in all planes and axes as discussed above for pessary devices 10 and 60.

Additionally, the electrode stimulating aspect of pessary device 100 may be combined with the inflation of a distendable membrane of either pessary device 10 or 60. Such combination of electrical stimulation to induce contraction of the urethra and mechanical localized pressure to contract the urethra provides for increased flexibility in controlling the amount of continence effort achieved. Additionally, the two modes may be alternated back and forth, allowing the tissues to rest from one modality while remaining under continence control with the other modality.

Electrical stimulation may be achieved using a number of different modalities known in the art. The concept uses parameters and variables of electrical stimulation that vary the size, shape and time of the electrical stimulation. Generally, the range for amplitude is usually in the milliampere range using a square shaped discharge wave and having a duty cycle of about 1:1, or 50%. The present invention anticipates using any number of variations for the above parameters and includes the option of varying the pattern and number of electrodes used to alter the field effect of the electrical stimulation.

Figure 9:
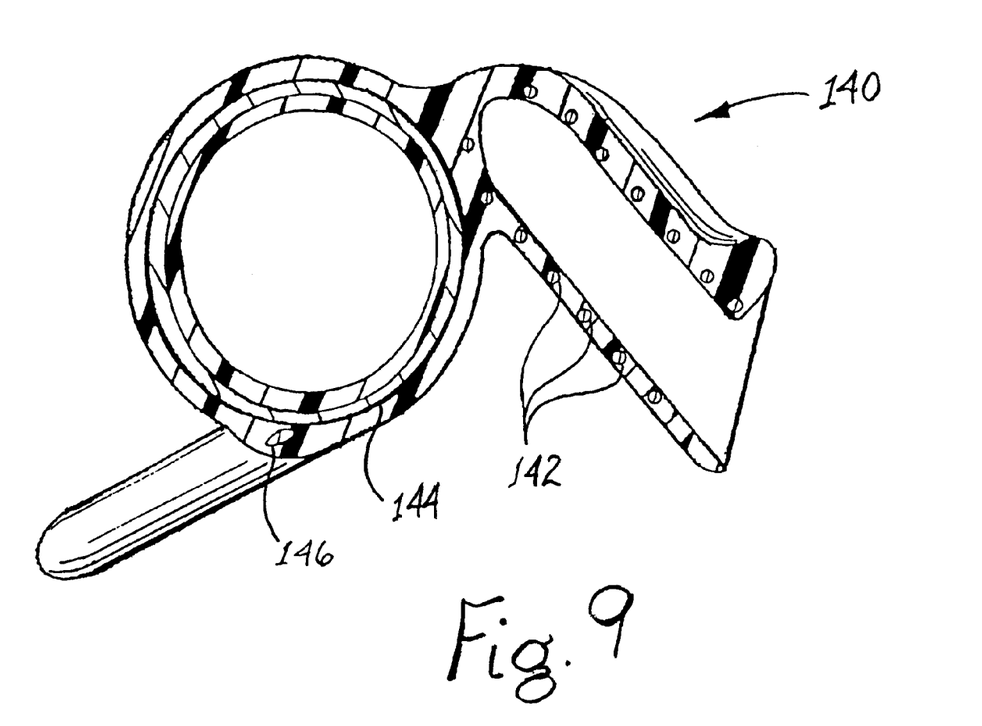
FIG. 9 is a cross-sectional view similar to the views of FIGS. 3, 6, or 8, depicting another alternative embodiment of the present invention.

FIG. 9 depicts an alternative structure for any one or all of the above depicted pessary devices wherein a pessary device 140 may be constructed from a resilient or semi-rigid polymeric material, for instance, "hard" elastomeric silicone, and the various main components are further supported structurally from within by internal flexible metal support rings 142, a band 144, and/or a rod 146. Metal bands may be used instead of metal rings, and vice versa. The substitution of metal rods for bands or rings is also anticipated. Some or all of the various flexible metal components may be used depending on the extent of resiliency and support desired. These additional resilient metal components may be added in part, or in whole, to any of the other embodiments discussed and depicted herein.

The foregoing description is considered as illustrative only of the principles of the invention, since numerous modifications and changes will readily occur to those skilled in the art. Consequently, it is not desirable to limit the invention to the exact construction and operation shown and described herein. Accordingly, all suitable modification and equivalents may be resorted to, falling within the scope of the present invention.

I claim:

1. An incontinence pessary device for use within a vaginal vault of a woman, the incontinence pessary device comprising:
   a resilient main support body having a primary plane of orientation and at least responsive to forces oriented along the main plane;
   at least two resilient lateral support bodies projecting from a position on the main support body toward generally opposite sides of the main support body in a secondary plane generally perpendicular to the primary plane, the at least two resilient lateral support bodies being at least responsive to forces oriented along the secondary plane; and
   a suburethral support body having a longitudinal axis of orientation in the primary plane and forming an obtuse angle to the secondary plane and having a contact surface elongated along the longitudinal axis, for engaging the mucosa and periurethral tissues of the vaginal vault of the woman, the suburethral support body projecting from a position on the main support body generally opposite the position of projection for the at least two lateral support bodies.

2. The invention of claim 1 in which the main support body comprises a polymer.

3. The invention of claim 2 in which the polymer comprises a polymer selected from a list of polymers consisting of: elastomeric silicone, polyethylene, polypropylene, polyester, polyurethane, poly(vinyl chloride), polyisobutylene, polychloroprene, polybutadiene, and copolymers of this list.

4. The invention of claim 3 in which the at least two lateral support bodies comprises a polymer and the polymer of the at least two lateral support bodies is the same polymer of the main support body.

5. The invention of claim 4 in which the at least two lateral support bodies include imbedded flexible metal rods.

6. The invention of claim 3 in which the suburethral support body comprises a polymer and the polymer of the suburethral support body is the same polymer of the main support body.

7. The invention of claim 6 in which the suburethral support body includes at least one imbedded flexible metal circular ring.

8. The invention of claim 3 in which the main support body includes an imbedded flexible metal circular band.

9. The invention of claim 2 in which the suburethral support body comprises a polymer.

10. The invention of claim 9 in which the polymer of the suburethral support body is the same polymer of the main support body.

11. The invention of claim 9 in which the suburethral support body includes at least one imbedded flexible metal circular ring.

12. The invention of claim 2 in which the main support body includes an imbedded flexible metal circular band.

13. The invention of claim 2 in which the at least two lateral support bodies comprises a polymer.

14. The invention of claim 13 in which the polymer of the at least two lateral support bodies is the same polymer of the main support body.

15. The invention of claim 13 in which the at least two lateral support bodies include imbedded flexible metal rods.

16. The invention of claim 1 in which the suburethral support body includes two lateral prominences laterally positioned to either side of the contact surface and elongate along the longitudinal axis forming a hollow therebetween.

17. The invention of claim 1 in which the suburethral support body further comprises an inner cylinder in fluid communication with an expansion space beneath a distendable membrane on the contact surface of the suburethral support body and expansion means for expanding and retracting the distendable membrane by the movement of a fluid into and out of the expansion space.

18. The invention of claim 17 in which the expansion means comprises an adjustable plunger operably engaging and telescopically slidable within the rigid inner cylinder forming an inner chamber of the rigid inner cylinder for holding the fluid.

19. The invention of claim 18 in which the adjustable plunger is controllable by a ratchet and pawl mechanism between the adjustable plunger and the inner cylinder.

20. The invention of claim 17 in which the expansion means comprises a tube with a valve in fluid communication with the expansion space, the valve adapted to connect to a hand held syringe.

21. The invention of claim 17 in which the rigid inner cylinder further comprises at least one mucous vent through a side wall of the rigid inner cylinder.

22. The invention of claim 17 in which the suburethral support body further comprises an electrode array of at least two electrodes in the distendable membrane on the surface of the suburethral support body for providing electrical stimulation to mucosa, periurethral tissue and urethra of the woman, the at least two electrodes electrically connected to a power source and control circuit for energizing the at least two electrodes.

23. The invention of claim 22 in which the power source and control circuit are carried separately from the remainder of the incontinence pessary device.

24. The invention of claim 22 in which the suburethral support body includes two lateral prominences laterally positioned to either side of the contact surface and elongate along the longitudinal axis forming a hollow therebetween.

25. The invention of claim 17 in which the suburethral support body includes two lateral prominences laterally positioned to either side of the contact surface and elongate along the longitudinal axis forming a hollow therebetween.

26. The invention of claim 1 in which the suburethral support body further comprises an electrode array of at least two electrodes in the surface of the suburethral support body for providing electrical stimulation to mucosa, periurethral tissue and urethra of the woman, the at least two electrodes electrically connected to a power source and control circuit for energizing the at least two electrodes.

27. The invention of claim 26 in which the power source and control circuit are carried separately from the remainder of the incontinence pessary device.

28. The invention of claim 26 in which the suburethral support body includes two lateral prominences laterally positioned to either side of the contact surface and elongate along the longitudinal axis forming a hollow therebetween.

29. The invention of claim 1 in which the main support body includes an imbedded flexible metal circular band.

30. The invention of claim 1 in which the at least two lateral support bodies include imbedded flexible metal rods.

31. The invention of claim 1 in which the suburethral support body includes at least one imbedded flexible metal circular ring.

32. The invention of claim 1 in which the suburethral support body includes at least one mucous vent.

* * * * *